United States Patent [19]

Thompson et al.

[11] 3,949,612

[45] *Apr. 13, 1976

[54] LIQUID SAMPLING

[75] Inventors: Richard R. Thompson; Malcolm F. Irwin, both of West Chester, Pa.

[73] Assignee: Pro-Tech Inc., Malvern, Pa.

[ * ] Notice: The portion of the term of this patent subsequent to Jan. 28, 1992, has been disclaimed.

[22] Filed: Jan. 27, 1975

[21] Appl. No.: 544,417

Related U.S. Application Data

[63] Continuation of Ser. No. 412,278, Nov. 2, 1973, Pat. No. 3,862,575.

[52] U.S. Cl. .............................. 73/421 B; 417/145
[51] Int. Cl.² ......................................... G01N 1/14
[58] Field of Search .................... 73/421 B; 417/145

[56] References Cited
UNITED STATES PATENTS

| | | |
|---|---|---|
| 1,780,538 | 4/1930 | Redfield .............................. 137/102 |
| 3,750,477 | 8/1973 | Rutowski ........................... 73/421 B |
| 3,751,983 | 8/1973 | Rutowski ........................... 73/421 B |
| 3,862,575 | 8/1973 | Thompson .......................... 73/421 B |

*Primary Examiner*—S. Clement Swisher
*Attorney, Agent, or Firm*—Charles A. McClure

[57] ABSTRACT

Successive samples are taken periodically from a body of liquid with the aid of pressurized fluid serving as both timing medium and sample propellant. Alternative high-pressure and low-pressure paths for the fluid correspond to high-lift and low-lift uses in sampling apparatus adjustable as to interval between successive samples and duration of taking of each sample, as well as convertible between levels of sample lift.

6 Claims, 1 Drawing Figure

U.S. Patent   April 13, 1976   3,949,612
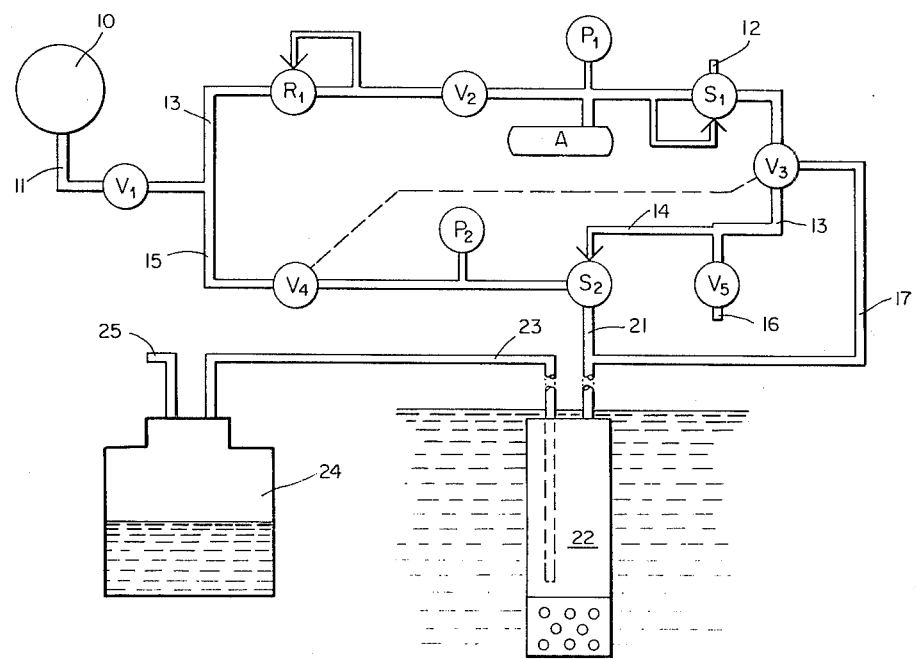

LIQUID SAMPLING

This is a continuation of application Ser. No. 412,278, filed Nov. 2, 1973, now U.S. Pat. No. 3,862,575.

This invention relates to sampling a liquid medium such as preliminary to determination of the composition thereof or of contaminants therein, concerning especially such sampling accomplished by use of a pressurized fluid for sample propulsion.

Manual techniques for sampling a medium for analysis or related purposes are giving way to automatic sampling, often electrically operated. Devices for setting frequency of sampling include spring-driven and electrical timing devices. Electrical operation is hazardous in an explosive atmosphere, such as may be encountered in oil refineries and other industrial operations, in sewers and sewage treatment plants, and in pollution-ridden areas. Electrical power lines are not available at remote sampling sites, and batteries often are cumbersome or otherwise unsatisfactory and require frequent replacement. Spring-winding is inconvenient, and spring motors are a source of maintenance requirements.

A primary object of the present invention is provision of a system for fluid energized sampling of liquid at either high or low pressure, corresponding to either high or low lift thereof to sample collection location.

Another object is flow-regulated control of sampling interval and sample duration in such a system irrespective of which pressure level is being used for sample propulsion.

A further object is accomplishment of the foregoing objects by means of relatively simple apparatus.

Other objects of this invention, together with means and methods for attaining the various objects, will be apparent from the following description and the accompanying schematic drawing of a preferred embodiment thereof, which is presented by way of example rather than limitation.

In general, the objects of the present invention are accomplished by providing timing circuitry for attachment to a source of fluid under pressure and by providing alternative high and low pressure paths for the fluid in propelling samples from a body of liquid to be sampled. The apparatus of this invention is adjustable as to interval between successive samples and the duration of taking of each sample, by control of flow rates of the pressurized fluid, and is convertible from high to low lift of samples by selection of appropriate fluid pressure level.

Source 10 of pressurized fluid connects via line 11, which conveniently contains primary on-off valve $V_1$, to two parallel branch lines, which may be viewed as low-pressure and high-pressure conduits, respectively.

First or low-pressure conduit 13 contains, in sequence, pressure regulator $R_1$, first flow-regulating valve $V_2$, pressure-responsive switching valve $S_1$, two-position outlet valve $V_3$, and finally second flow-regulating valve $V_5$, whose outlet 16 vents to the atmosphere. Accumulator tank A and low-pressure gauge $P_1$ are interconnected to the first conduit between the first flow-regulating valve and the pressure-responsive switching valve. The latter valve normally closes the conduit at its location but vents the downstream portion thereof via vent 12 thereof; it is responsive to the fluid pressure in the immediately upstream portion of the conduit, which interconnects directly to the accumulator tank and the pressure gauge, and opens at a predetermined pressure (simultaneously closing the vent) and recloses at a lower predetermined pressure.

Second or high-pressure conduit 15 contains secondary on-off valve $V_4$, which is ganged mechanically (as indicated by broken lines) for actuation simultaneously with dual-outlet valve $V_3$ so as to be on or open when valve $V_3$ is closed to the portion of second conduit 15 downstream therefrom and is open to conduit 17, which bypasses valve $V_5$ and switching valve $S_2$ to connect directly to line 21 to sample intake chamber 22. In the off or closed position of secondary switching valve $S_2$ the connection of dual-outlet valve $V_3$ is reversed, i.e., open to the downstream portion of conduit 13 and closed to the bypass conduit 17. Pressure gauge $P_2$ is connected to the downstream portion of the second conduit, which terminates in normally closed second pressure-responsive switching valve $S_2$ connected to sense and be responsive to (i.e., opened at a given level of) the pressure in the portion of first conduit 13 downstream from valve $V_3$ and upstream from valve $V_5$.

As shown connected for use, the outlet of switching valve $S_2$ is connected via line 21 to sample intake chamber 22 submerged in the body of liquid to be sampled. From the sample intake chamber, sample line 23 (with dip tube portion shown is broken lines inside the chamber) leads to sample collection container 24, which has vent tube 25 to the atmosphere. The sample chamber has a check valve (not shown) that enables liquid to enter the chamber, but when fluid under pressure is received via line 21 the check valve is forced shut and the liquid inside is propelled via line 23, therefrom into collection vessel or sample container 24, and propellant fluid is vented through vent 25 of the sample container.

Operation of the apparatus of this invention is readily understood by reference to the foregoing description and the accompanying illustration thereof.

With primary on-off valve $V_1$ in the on position and secondary on-off valve $V_4$ in the off position, fluid under pressure from source 10 flows through line 11 into branch line 13, being the first or low-pressure conduit. Reduced to a predetermined pressure by pressure regulator $R_1$, the fluid flows on through the line at a rate determined by the setting of first flow-regulating valve $V_2$ and the pressure downstream therefrom, as indicated on low-pressure gauge $P_1$. The fluid collects at gradually increasing pressure, principally in accumulator tank A, until the switching pressure of normally closed first pressure-responsive switching valve $S_1$ is reached. Thereupon the valve switches to the open position and releases the accumulated fluid to flow downstream through bypass conduit 17 outlet of dual-outlet valve $V_3$ directly to sample intake chamber 22, from which it forces the liquid contents to sample collection container 24 at the relatively low accumulated fluid pressure. Venting of fluid from vent 25 of the collection container reduces the pressure in the first conduit substantially, whereupon first switching valve $S_1$ recloses and vents to atmosphere the path to the sample chamber, which then takes in another sample. Pressure again builds up in the accumulator tank, and the sampling cycle repeats itself.

With secondary on-off valve $V_4$ in the alternative or on position, however, the action is the same only until the accumulated pressure opens the first switching valve. Now dual-outlet valve $V_3$ is closed to the bypass line and open to the downstream portion of first conduit 13, through which the fluid then proceeds to and through second flow-regulating valve $V_5$ to the atmosphere at a rate controlled by the setting thereof. The surge of fluid into the downstream part of the first conduit located between the dual-outlet valve and the second flow-regulating valve is sensed via sensing line 14 to normally closed second pressure-responsive switching valve $S_2$, which itself is located at the terminus of second or high-pressure conduit 15. The resulting opening of the latter switching valve permits fluid to flow through the latter conduit at such high pressure, indicated on second pressure gauge $P_2$, into line 21 to propel the contents of sample intake chamber 22 to the collection container. When second flow-regulating valve $V_5$ has reduced the pressure accumulated in the first conduit to the reclosing pressure of first switching valve $S_1$, the reclosing thereof and the consequent venting of the downstream portion of the first conduit through $S_1$ vent 12 drops the pressure sensed by second switching valve $S_2$, which also recloses, whereupon the high-pressure sampling cycle repeats itself.

Thus, in both low-pressure and high-pressure operation, first flow-regulating valve $V_2$ mainly determines the interval between successive samples and second flow-regulating valve $V_5$ determines the duration of the time over which each sample is taken, which usually is much shorter than the period between successive samples. The pressure in the low-pressure line is conveniently reduced by the first pressure regulator to about one atmosphere, and the low-pressure switching valve set to open at about 16 psi and to reclose at about 14 psi, for example. The high-pressure switching valve may open at not so high a pressure (e.g., 15 psi) and reclose at a somewhat lower pressure (e.g., 5 or 10 psi). Alternatively, the respective switching valves could be set so that the band through which the low-pressure valve operates is broader than that through the high-pressure valve operates (e.g., first valve to open at 25 psi and reclose at 10 psi, high-pressure valve to open at 20 psi and reclose at 15 psi) but this is not preferred because of the excessive venting of fluid by the timing circuitry and perhaps unduly short resulting sample duration.

The source of fluid under superatmospheric pressure may be located internal or external to the apparatus. The fluid source may comprise a reservoir of suitable fluid, such as nitrogen, helium, or other gaseous medium that is inert relative to the body of liquid and preferably also to any chemical tests to be performed upon the samples propelled thereby from the body of liquid. If air is not objectionable as a propellant, the source may be a tank of compressed air or a line from an air compressor wherever located. The lift available at low-pressure operation is about 30 feet of water (at about one atmosphere switching pressure of $S_1$); the lift at high-pressure operation is determined by the source pressure, which may be hundreds of pounds per square inch. By adjusting the setting of pressure regulator for the source (usually part of the source apparatus) the operator of this apparatus can adapt it readily to different lift requirements. Thus, for a 100 ft. deep well the source pressure (of perhaps 250 psi) may be dropped to about 50 psi.

Conventional materials of construction inert to the liquid being sampled are suitable for the various valves and other components. The flow-regulating valves, in addition to controlling the flow of fluid therethrough, may comprise visual indicators of flow rate, as by means of one or more balls or similar floats in a tapered tube as illustrated (e.g., FIG. 2) and described in U.S. Pat. No. 2,720,109. The pressure-responsive switching valves may be of the W-spring type shown (e.g., FIG. 5) and described in that patent or may be of the ball-controlled type shown (e.g., FIGS. 2a, 2b, 3a, 3b) and described in U.S. Pat. No. 3,751,983 or other suitable construction. The sample chamber conveniently is constructed as shown (FIGS. 6 and 5, respectively) and described in each of those patents.

Although only a single embodiment of this invention has been described and illustrated here, modifications may be made therein, as by adding, combining, or subdividing parts or steps, or by substituting equivalents, while retaining distinctive advantages and benefits of the present invention, which itself is defined in the following claims.

What is claimed is:

1. Liquid-sampling procedure operable from a source of propellant fluid under high pressure to collect samples of liquid from a body thereof, wherein such fluid is utilized as both a sample propellant and as a timing medium for controlling the interval of time between successive samples, and convertible between low-pressure and high-pressure propulsion of samples, comprising establishing a low-pressure path and a high-pressure path from the source of pressurized fluid, accumulating fluid temporarily in the first path for timing intervals between successive samplings, and releasing the accumulated fluid during each sampling at the end of each such interval; releasing the accumulated fluid to propel samples from the body of liquid therewith during low-pressure operation, alternatively releasing fluid directly from the propellant source to propel samples from the body of liquid therewith during high-pressure operation, and exhausting the accumulated fluid at low pressure to the atmosphere during high-pressure propulsion of samples.

2. Liquid-sampling procedure according to claim 1, wherein the low-pressure path is normally closed midway of its length below a given accumulated pressure and is vented downstream therefrom, being adapted to open and stop venting at a given increment in accumulated pressure.

3. Liquid-sampling procedure according to claim 2, wherein the high-pressure path is normally closed to the body of liquid being sampled and is adapted to open at such given incremented pressure in the low-pressure path during each sampling.

4. Liquid-sampling procedure convertible between low-pressure and high-pressure propulsion of liquid samples from a body of liquid, utilizing gaseous fluid from a source thereof under relatively high pressure, comprising establishig from the source of such fluid a first path having a normally open inlet but normally closed intermedite its inlet and outlet, the outlet communicating with the body of liquid being sampled at low-pressure propulsion to propel samples therefrom and communicating with the atmosphere at high-pressure propulsion, establishing from the fluid a normally closed second propulsion path from the fluid source to the liquid being sampled, reducing the fluid pressure at the inlet to the first path to a value that is low relative to the source pressure but that is above atmospheric pressure, controlling the flow of fluid continuously from the source into the inlet of the first path for accumulation therein at a pressure gradually rising toward such value, intermittently releasing such accumulated fluid at a given pressure value to and out of the outlet of the first path, to propel samples therefrom at low-pressure propulsion and to be dissipated in the atmosphere at high-pressure propulsion, and reclosing the first path when the accumulated fluid pressure falls to a lower given value.

5. Liquid-sampling procedure according to claim 4, wherein high-pressure propulsion includes opening the second path from the pressure source directly to the body of liquid and thereby propelling samples therefrom whenever the accumulated pressure of fluid reaches a given value and reclosing the path whenever the pressure accumulated in the first path falls to a preselected lower level.

6. Liquid-sampling procedure according to claim 5, wherein the duration of propulsion at high pressure is controllable by adjusting the rate at which the accumulated fluid is exhausted to the atmosphere.

* * * * *